United States Patent [19]
Ishiguro et al.

[11] Patent Number: 5,875,027
[45] Date of Patent: Feb. 23, 1999

[54] SENSITIVITY CALIBRATION DISK FOR SURFACE DEFECT TESTER

[75] Inventors: Takayuki Ishiguro; Izuo Horai; Kazuya Tsukada, all of Kanagawa-ken, Japan

[73] Assignee: Hitachi Electronics Engineering Co., Tokyo, Japan

[21] Appl. No.: 48,993

[22] Filed: Mar. 27, 1998

[30] Foreign Application Priority Data

Mar. 28, 1997 [JP] Japan ................................ 9-095036

[51] Int. Cl.⁶ ............................................ G01J 1/02
[52] U.S. Cl. ................................. 356/243.4; 356/243.6; 356/243.8; 356/423
[58] Field of Search ..................... 356/243.4, 243.6, 356/243.8, 423

[56] References Cited

U.S. PATENT DOCUMENTS

| | | | |
|---|---|---|---|
| 4,346,996 | 8/1982 | Miller | 356/243.8 |
| 5,258,974 | 11/1993 | Ishimura et al. | 356/243.6 |
| 5,691,812 | 11/1997 | Bates et al. | 356/243.4 |

*Primary Examiner*—Frank G. Font
*Assistant Examiner*—Reginald A. Ratlff
*Attorney, Agent, or Firm*—Fay, Sharpe, Beall, Fagan, Minnich & McKee

[57] ABSTRACT

A calibration disk for calibrating a sensitivity of a surface defect tester, according to the present invention, comprises n (n is an integer equal to or larger than 2) false defect rows each including 3 or more false defects each formed in a radial or peripheral direction provided in the peripheral direction of the calibration disk at a predetermined angle pitch. The false defects of each false defect row take in the form of protrusions or recesses having substantially the same size, adjacent ones of the false defects are physically separated by a predetermined distance larger than a width of a laser spot and the false defects of a certain one of the false defect rows are different in size from the false defects of other false defect rows.

12 Claims, 4 Drawing Sheets

SENSITIVITY CALIBRATION DISK FOR SURFACE DEFECT TESTER

DESCRIPTION

1. Technical Field

The present invention relates to a sensitivity calibration disk for a surface defect tester and, particularly, to a sensitivity calibration disk for calibrating a detection sensitivity of a defect tester which can easily set an appropriate defect detection sensitivity correspondingly to a size of defect to be detected.

2. Background Art

A semiconductor wafer or a hard magnetic disk used as a recording medium of a computer system is tested on surface defect and size thereof in some of the fabrication steps thereof. That is, the test on the surface defect of a disk is performed in various fabrication steps, for example, in a state of a polished disk substrate, in a state of a disk plated with a metal and in a state of a magnetic disk having a magnetic thin film thereon obtained by painting the metal plated disk with a magnetic material, etc.

Figure 5A:
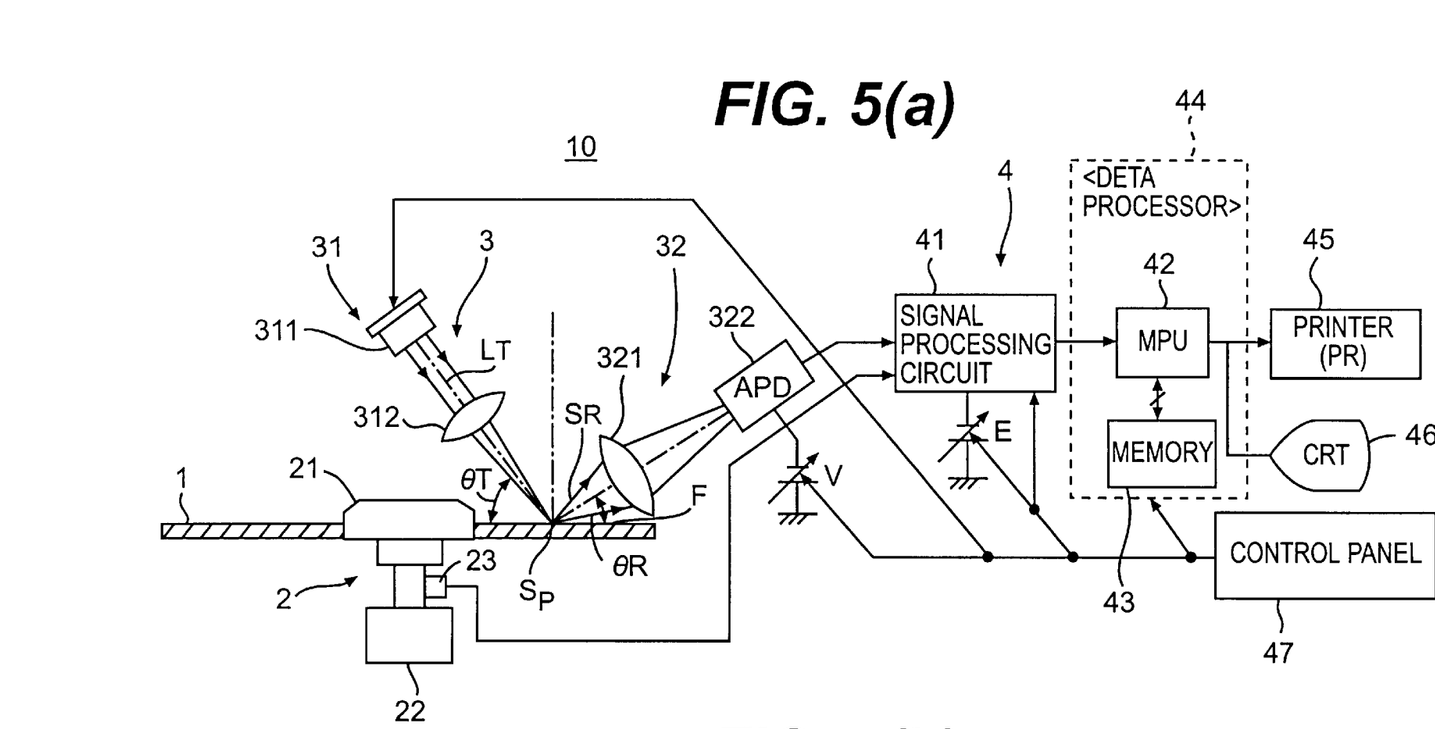
FIGS. 5(a) and 5(b) show a construction of a main portion of the magnetic disk defect tester and a laser spot thereof, respectively.

FIG. 5(a) shows a main portion of a surface defect tester for detecting surface defects of a magnetic disk.

In FIG. 5(a), the surface defect tester 10 is constructed with a rotary mechanism 2, an optical detection system 3 and a defect detector 4. A disk 1 to be tested is mounted on a spindle 21 of the rotary mechanism 2 and rotated by a motor (M) 22. The optical detection system 3 is constructed with a light projection system 31 including a laser light source 311 and a condenser lens 312 and a optical light receiving system 32 including a condenser lens 321 and a light receiver 322. A laser beam LT produced by the laser light source 311 is condensed by the condenser lens 312 to a laser spot Sp on a surface of the disk 1.

Figure 5B:
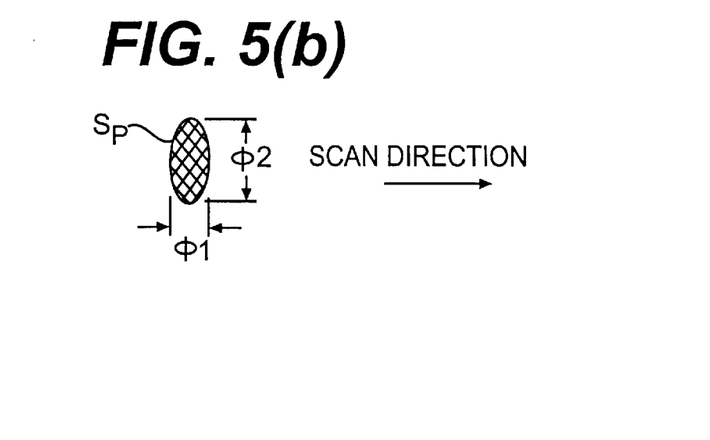

By moving the spot Sp in a radial direction R of the disk 1 while rotating the disk 1, the laser spot Sp scans the surface of the disk 1 coaxially or spirally. In this case, in order to make a total scan time of the disk 1 as short as possible, an area of the laser spot Sp is made ellipsoidal having a length $\phi 1$ in a minor axis direction and a length $\phi 2$ in a major axis direction as shown in FIG. 5(b). The major axis is arranged in the radial direction of the disk to increase a scan width of the laser spot in the radial direction.

The laser spot Sp is scattered by a defect F on the surface of the disk 1. A scattered light SR is condensed by the condenser lens 321 of the optical light receiving system 32 and the condensed scattered light is received by the light receiver 322 composed of an opto-electric conversion element such as an avalanche photo-diode (APD) or a photo-multiplier tube (PMT). An output of the light receiver 322 is input to a signal processing circuit 41 of the defect detector 4 and the defect F is detected by a defect detection signal output from the signal processing circuit 41. The size of the defect F is detected according to an amplitude of the output signal of the light receiver 322, that is, the detection signal.

The signal processing circuit 41 includes an amplifier for amplifying the output signal of the light receiver 322, a sampling circuit for sampling the amplified output signal corresponding to a defect which is larger than noise component of the output signal with a pulse supplied from a rotary encoder 23 and storing a peak value of the sampled output signal as a level value of the detection signal of the defect as a detected defect value, an A/D converter for digitizing the sampled peak value and a position data producing circuit responsive to the pulse from the rotary encoder 23 for producing a position data on the disk, etc.

The signal processing circuit 41 simultaneously sets a plurality of different threshold values for the output signal output from the light receiver 322 and detects the size of defect according to the level of the output signal which exceeds any one of the threshold values. In this case, when the threshold values are set in stepwise finely, the size of defect corresponds to the output signal value and, when the threshold values are relatively roughly set, defects having various sizes are detected as those fallen in a certain class. The detection value is output as a digital value and the position data producing circuit produces data of the detection value indicative of the defect size or the classified defect size and position data thereof.

The digital size data of the respective defects, that is, the data of detected defect value, and the digital position data thereof on the disk are supplied from the signal processing circuit 41 to a data processor 44. The data processor 44 is composed of a MPU 42 and a memory 43, etc. The number of defects of each size are counted in the data processor 44 and the size data and the count value of the defects, etc., are output to a printer (PR) 45 together with the position data of the defects on the disk 1. In this case, these data may be printed out as a map on the disk. Further, the position data is displayed on a screen of a display (CRT) 46, etc., as a map on the disk. The count value of the defects in each class of size is also displayed on the screen separately. When the data processor 44 receives the detected defect value from the signal processing circuit 41, a classification processing produces the size data of defect by classifying the detected defect value according to the size of defect internally. It should be noted that the term "size" used in this specification means a size of defect in plan view and a depth or height thereof.

Figure 6:
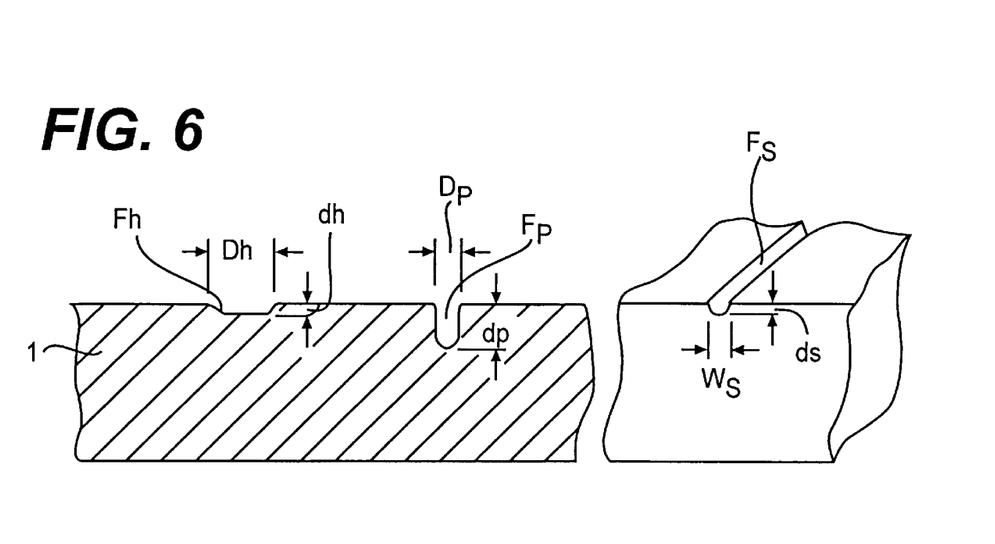
FIG. 6 illustrates various defects which may exist on a surface of a magnetic disk.

The defect F on the disk 1 may have various sizes and an example thereof is shown in FIG. 6.

In FIG. 6, a defect Fh takes in the form of a shallow pit or saucer pit and has a relatively large diameter Dh and has a depth dh smaller than the diameter Dh. A defect Fp takes in the form of a deep well having a relatively small diameter Dp and a large depth dp and is usually called as merely a pit. The defects Fh and Fp usually exist discretely. A defect Fs takes in the form of a groove and is called as scratch defect. Such scratch defect may have various width ws and depth ds. There may be other defects having other shapes and sizes than those mentioned above. Further, there may be defects called extraneous substances having various sizes. Such extraneous substance may be fine particles attached onto the surface of the disk 1.

In order to detect defects having various shapes and sizes, the defect tester 10 regulates the detection sensitivity for defects by appropriately setting parameters related to the level of detection signal, such as a projection angle $\theta T$ of the laser beam LT of the optical projection system 31, a light receiving angle $\theta R$ of the light receiving system 32, a voltage V applied to the light receiving element, that is, the avalanche photo diode APD, a gain of the amplifier provided within the signal processing circuit 41, a threshold voltage E for removing noise and the laser output of the laser light source 311, etc., through the control panel 47 including the control circuit.

As mentioned previously, the size of defect is determined by not only the area but also the depth or the height (volume).

The defect detection sensitivity of the surface defect tester 10 is optimally set for each of various defects F. However, the regulation of sensitivity requires skills. Particularly, it is very difficult to regulate the sensitivity such that the tester can detect shallow defect to deep defect or can detect small extraneous substance to large extraneous substance. Further, it is impossible to obtain defect data by which the size of defect can be correctly classified, unless the regulation of defect detection sensitivity is calibrated according to a constant reference. Further, defect detection data of various sizes of defects or various classified sizes of defects vary under influence of setting conditions of the tester. Further, there is a tendency that a variation of defect detection data occurs between different testers, causing a common use of the defect detection data to be difficult.

The calibration of the detection sensitivity of the conventional tester is performed by using disks which have shallow pit, pit and scratch which have known sizes corresponding to defects to be detected and sizes thereof as sample defects or disk which have extraneous substances having specific heights, as sample disks and detecting the defects of the respective sample disks. However, since the defects of the respective sample disks have specific shapes of specific sizes, there may be cases where the detection sensitivity calibrated thereby becomes not appropriate in view of a range of classified size of defects to be detected and there may be deviation of the detected size or the classification. Further, it is practically impossible to known the preciseness of the classification of defect size in the surface defect test.

With the recent increase of recording density of a disk, the range of size of defect to be detected is reduced or there is a tendency that the defect detection is directed to a smaller size. However, it is very difficult to obtain sample disks for detection sensitivity calibration which are appropriate for the classification of sizes.

SUMMARY OF THE INVENTION

An object of the present invention is to provide a calibration disk for calibrating a sensitivity of a surface defect tester, with which an appropriate defect detection sensitivity corresponding to a size of defect to be detected can be easily set.

In order to achieve the above object, a calibration disk for calibrating a sensitivity of a surface defect tester according to the present invention is featured by that n (n is an integer equal to or larger than 2) false defect rows each including 3 or more false defects arranged radially or peripherally of the calibration disk are formed with a predetermined angular space, the false defects of each false defect row take in the form of protrusions or recesses having substantially the same size, adjacent ones of the false defects of each false defect row are physically separated from each other by a predetermined distance larger than a width of a laser spot and the false defects of a certain one of the false defect rows are different in size from the false defects of other false defect rows.

When an operator performs a defect test by using a surface defect tester shown in FIG. 5 with using this sensitivity calibration disk as an object to be tested and displays a result of test, that is, detection values of the size of defects detected correspondingly to levels of detection signals or a classified value of the defect size classified according to the level of the detection signal thereof, on a display device, the defects are displayed together with an image of the disk on the display device as a map. In this case, since at least an image corresponding to false defects having different sizes is obtained, it is possible to regulate the sensitivity of the surface defect tester such that an image corresponding to an appropriate detection sensitivity is obtained, while watching the thus obtained image on the display device.

Therefore, it is possible without skills to appropriately regulate the detection sensitivity for the size classification of defect while watching the image of the calibration disk on the display device. Further, since it is possible to reproduce the setting condition of the defect detection sensitivity of the surface defect tester so long as the same calibration disk is used, a test result data is hardly influenced by the setting condition and a variation of data is reduced. Of course, such variation of detection result data hardly occurs even between different surface defect testers and a common use of the data becomes possible between different surface defect testers.

Particularly, when the size of the false defects of the respective false defect rows increases or decreases in stepwise in a certain direction, a false defect row corresponding to each size is displayed. In this case, the image of the false defect rows displayed correspondingly to the regulation of the detection sensitivity becomes different.

Therefore, it is possible to appropriately regulate the detection sensitivity correspondingly to the size classification of the defect to be detected, while watching the image of the false defect displayed on the display screen.

Particularly, it is possible to regulate the detection sensitivity of the surface defect tester for a defect whose size is substantially an intermediate of the size classification. In such case, it is possible to know sizes which can fall within a class correspondingly to the sensitivity regulation from the displayed condition of the false defects on the display screen.

Further, in this case, it is also possible to classify the sizes of defects in a detectable size range of the false defects in the false defect row, which are obtained by watching the image of the false defects displayed on the screen. This can be realized as follow: For example, a relation between the level of the detection signal and the classified sizes of the false defects of the false defect row is extracted on the basis of the data obtained when the surface defect test for the calibration disk is performed by a data processor 44 shown in FIG. 5 and the size classification is performed by applying the extracted relation to the level of the detection signal obtained by the disk test. With this, it is possible to substantially correctly calibrate data indicative of size of a defect or data indicative of classifications of sizes of defects detected by the disk defect tester.

By performing the calibration of detection sensitivity to the surface defect tester at every start time of test or similarly applying the calibration to a number of other surface defect testers, a variation of detection sensitivity and/or test result data which may occur in every test or a variation of detection sensitivity or test result data which may occur between the testers can be restricted.

As a stepwise selection range of size of the respective false defects of a false defect row, which may take in the form of protrusions or recesses, it is preferable that a length of one side thereof is within a range from 0.5 $\mu$m to 20 $\mu$m and a depth or height in a range from 0.01 $\mu$m to 0.75 $\mu$m when the shape of the false defect is square or rectangular. When the shape of the false defect is circular, it is preferable that a diameter is within a range from 0.5 $\mu$m to 20 $\mu$m and a depth or height is within a range from 0.01 $\mu$m to 0.75 $\mu$m.

DESCRIPTION OF THE PREFERRED EMBODIMENTS

Figure 1A:
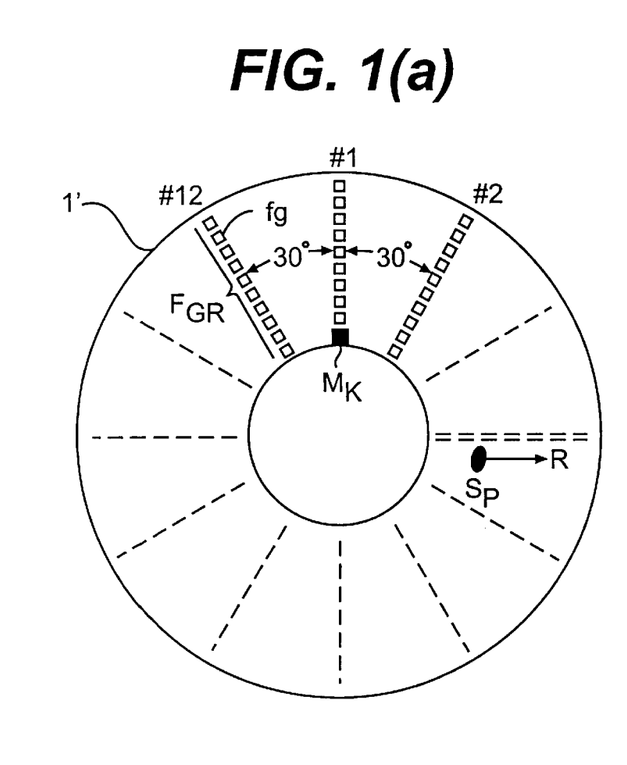
FIG. 1(a) is a plan view of a sensitivity calibration disk of a magnetic disk surface defect tester, according to an embodiment of the present invention, showing an arrangement of false defect rows thereon.

A sensitivity calibration disk (referred to as "reference disk", hereinafter) 1a shown in FIG. 1(a) is a disk made from an aluminum disk having mirror polished surfaces. The aluminum disk is put in a target position of an ion beam sputtering device and a desired false defect in the form of a recess is formed by sputtering a position of the aluminum disk corresponding thereto with ion beam. By forming a number of pits in a specific row in this manner, a row of false defects are formed. Such false defect may be formed by melting a portion of the disk surface by laser beam. In the latter case, the false defect may be a circular pit. Alternatively, false defects in the form of recesses can be formed by etching with using a resist as a mask.

On the other hand, false defects in the form of protrusions may be formed by adhering particles sputtered from the target by an ion beam sputtering device to the aluminum disk through a mask having a plurality of holes. In this case, a metal material of the target is preferably tungsten. The false defects in the form of protrusions may be selectively formed along a radial direction or peripheral direction of the aluminum disk by epitaxially growing aluminum by VCD through a photo resist.

Figure 1B:
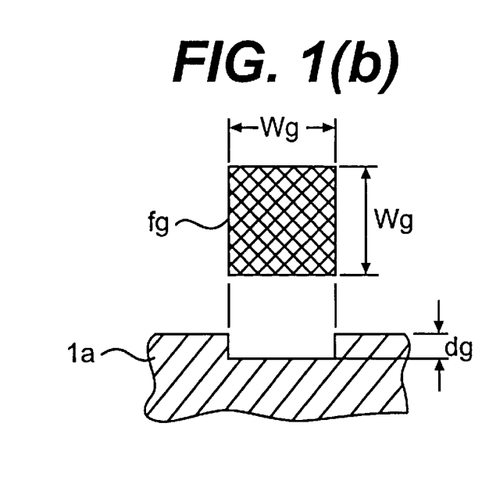
FIG. 1(b) shows a false defect of a false defect row which takes in the form of a square recess.

As shown in FIG. 1(a), for example, 12 false defect rows #1, #2, ..., #12 each including a number of false defects fg in the form of recesses may be formed along equiangularly spaced 12 radial directions by the ion beam sputtering device. The false defects fg take in the form of square recesses having the same size. The size of the false defect fg is controlled by controlling the amount of ion beam, the mass of particle used, the time of ion beam bombardment and the sputtering position, etc. Cross sectional diameter of ion beam used in this case is about one fourth to one tenth of a length of one side of a square false defect. A plurality of positions along one of the lateral sides of the square recess to be formed are bombarded with ion beam and the bombardment is repeated while in stepwise shifting the ion beam vertically. For example, in a case where a false defect in the form of a square recess having one side length wg of 1 $\mu$m, at least 5 points along one lateral side of the false defect to be formed are bombarded with ion beam having a cross sectional diameter of, for example, 0.2 $\mu$m. Then, the ion beam is shifted vertically by 0.2 $\mu$m and 5 points along a direction parallel with the lateral direction are bombarded with the same beam. This procedure is repeated through 4 vertical shifts of the ion beam and the total of 25 ion beam bombardments result in the false defect fg in the form of the square recess having one side length of 1 $\mu$m as shown in FIG. 1(b). This processing is repeated a plurality of times corresponding to the number of false defects along each of the 12 radial directions of the disk 1a to form the false defects with a pitch larger than a radial width (major axis length) $\phi$2 of the laser spot Sp. A position of the false defect to be formed next in the peripheral direction which is the scan direction of the laser spot Sp is, of course, remote from a preceding false defect by a distance much larger than the peripheral width (minor axis length) $\phi$1 of the laser spot Sp.

A mark Mk provided on an inner periphery of the false defect row indicates that false defect row is a reference false defect row #1. The mark Mk is provided as a false defect having a shape desired as a mark having a size larger than the other false defects. In this embodiment, the respective false defect rows are formed such that the size of false defects of the rows which are on a certain radial position increases with positions thereof along a clockwise direction, so that a group FGR of the false defects fg having different size can be identified. Incidentally, it should be noted that the increase of the defect size along the clockwise direction means a reduction of the defect size in the counterclockwise direction. Therefore, the increase and reduction are a relative matter.

Although, in FIG. 1(a), the false defects of only the false defect rows #1, #2 and #12, which take in the form of the square recesses are shown, it should be noted that the side widths Wg and the depths dg (FIG. 1(b)) of the false defects are increased in stepwise from the false defect row #1 to the false defect row #12. However, since differences in side width and in depth between the false defects of adjacent false defect rows are so small that it is very difficult to illustrate such differences clearly, the size of the false defects including the depth thereof is shown as substantially the same in FIG. 1(a).

The ranges of the side length wg and the depth dg of the false defect fg shown in FIG. 1(b) may be as follows although other ranges may be used:

Size of False Defect fg
 wg: 0.5 $\mu$m, 1 $\mu$m, 3 $\mu$m, 5 $\mu$m, 10 $\mu$m, 20 $\mu$m
 dg: 0.025 $\mu$m, 0.05 $\mu$m, 0.2 $\mu$m, 0.75 $\mu$m The ranges of the side length wg and the depth dg mentioned above are enough to cover the side length and depth of the practical defect size.

In a case where the size of defects is classified with using the defect side length of, for example, 1 $\mu$m as a center or reference, wg=1 $\mu$m, wg=0.5 $\mu$m and wg=3 $\mu$m are selected as the side lengths of false defects and used in such combinations as follows:

The side length wg of the false defects of the false defect row #1 is made 0.5 $\mu$m and the depth thereof is made 0.025 $\mu$m, those of the false defect row #2 are made 0.5 $\mu$m and 0.025 $\mu$m, respectively, the false defects of the false defect row #3 are made 0.5 $\mu$m and 0.02 $\mu$m, respectively, those of the false defect row #4 are made 0.5 $\mu$m and 0.025 $\mu$m, respectively, the false defects of the false defect row #5 are made 1 $\mu$m and 0.025 $\mu$m, respectively, those of the false defect row #6 are made 1 $\mu$m and 0.05 $\mu$m, respectively, the false defects of the false defect row #7 are made 1 $\mu$m and 0.2 $\mu$m, respectively, those of the false defect row #8 are made 1 $\mu$m and 0.75 $\mu$m, respectively, those of the false defect row #9 are made 3 $\mu$m and 0.025 $\mu$m, respectively, those of the false defects of the false defect row #10 are made 3 $\mu$m and 0.05 $\mu$m, respectively, those of the false defect row #11 are made 3 $\mu$m and 0.2 $\mu$m, respectively, and the false defects of the false defect row #12 are made 3 $\mu$m and 0.75 μm, respectively. The increase in depth of false defects of the respective false defect rows are 0.025×2, 0.025×4, 0.025×20 and 0.025×30 with 0.025 μm as a reference value.

The 12 false defect rows each having the false defects fg different in size from the other false defect rows are shown in FIG. 1(a). In FIG. 1(a), the size of the false defects in one row in an upstream in the clockwise direction is smaller in stepwise than that in a downstream in the clockwise direction.

In a case where the center size of defects to be classified is, for example, 5 μm, the reference disk 1a having 12 false defect rows including false defects whose one side sizes are 3 μm, 5 μm and 10 μm for respective depths is prepared.

Where the angular pitch of the false defect rows is 15°, it is possible to provide a reference disk having 24 false defect rows. Thus, the single reference disk can include both of the above mentioned two examples each including 12 false defect rows. That is, the false defect rows including false defects fg whose sizes are gradually increased every row are provided for each of the combinations of the above mentioned wg=0.5 μm, wg=1 μm, wg=3 μm, wg=5 μm, wg=10 μm and wg=20 μm.

Figures 2A, 2B:
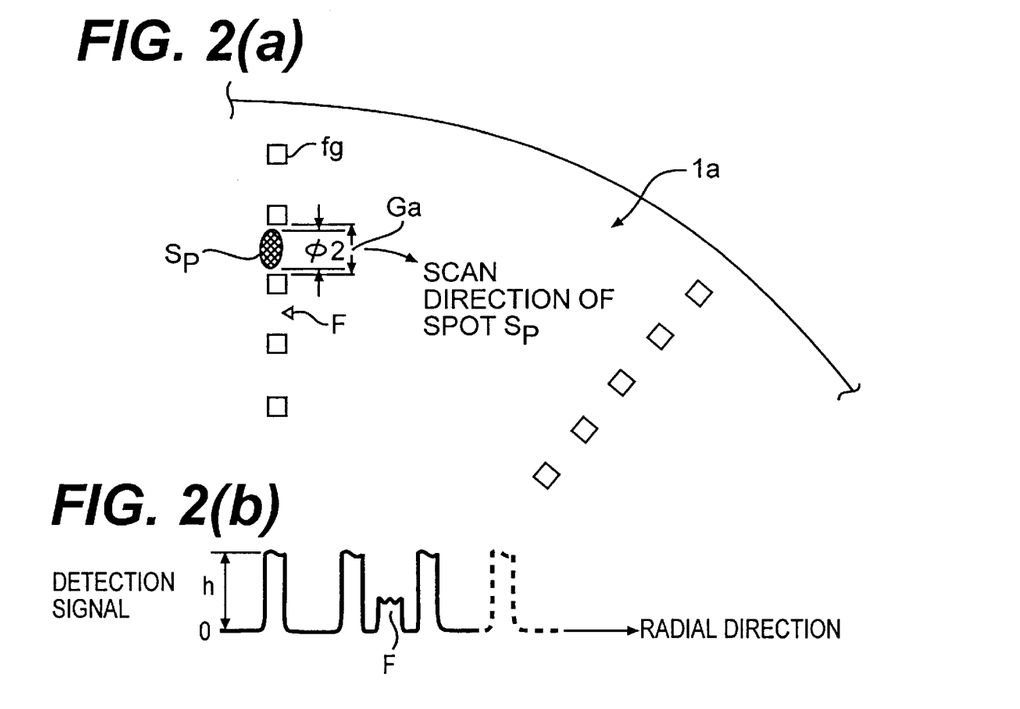
FIGS. 2(a) and 2(b) show a relation between a pitch of the false defects in a false defect row and a scanning laser spot and a detection signal of the false defect, respectively.

The false defects fg within each false defect row FGR are arranged equidistantly with the same gap Ga which is slightly larger than the major axis length (width in the radial direction of the disk) φ2 of the laser spot Sp, as shown in FIG. 2(a).

The defect test is performed by mounting such reference disk 1a in lieu of the disk 1 on the magnetic disk defect tester 10 shown in FIG. 5 and the defect size is displayed on the display device 46 by using the detection value of false defect detected correspondingly to the level of the detection signal or the classification value of defects classified correspondingly to the level of the detection signal, so that the false defect rows of the reference disk 1a is displayed on the display 46 as a defect map. The defect map displayed depends upon the detection sensitivity regulation. For example, when the detection sensitivity is set high, small size false defects are displayed as having the sizes thereof, while false defects whose sizes are larger than a certain size are displayed as having the same size since the size of false defects is changed in stepwise and the levels of detection signals thereof are saturated. On the contrary, when the detection sensitivity is set low, false defects having small sizes are not displayed since they are not detected, while false defects having large sizes are displayed as having the sizes thereof. According to the present invention, it is possible to regulate the detection sensitivity such that the optimal display is obtained by repeating the defect tests for the reference disk 1a a plurality of times while regulating the detection sensitivity through the control panel 47.

In this case, the regulation of the detection sensitivity of the tester is performed by regulating the voltage V applied to the light receiving element 322 (ADP), the gain and/or the threshold voltage E of the amplifier of the signal processing circuit 41 and/or the laser output of the laser light source 311, through the control panel 47. Further, the projection angle θT of the laser beam LT of the light projection system 31 and/or the light receiving angle θR of the light receiving system 32 may be regulated on demand.

For example, when the reference disk 1a having the 12 false defect rows as shown in 1(a) is tested by the defect tester 10 to classify the sizes of the false defects with using a defect having one side length of 1 μm as the reference size, it is possible to regulate the various parameters through the control panel 47 such that the detection sensitivity becomes suitable to clearly display the respective false defect rows #1 to #12.

Further, when the reference disk 1a having the 24 false defect rows is tested by the defect tester 10 as mentioned previously, it is enough to regulate the detection sensitivity by regulating the various parameters of the tester such that 12 of the 24 false defect rows which are selected correspondingly to the measuring sizes for the defect size classification are clearly displayed. Further, a variation of the detection data for every test can be reduced by displaying 12 false defect rows having preliminarily determined sizes and regulating the detection sensitivity at a start of every test, and, thus, it is possible to restrict a variation of the detection data between different surface defect testers.

When the detection sensitivity is set definitely for only one size range in this manner, it is possible to regulate the detection sensitivity through the control panel 47 such that the defect detection range corresponding to a size which is desired to be displayed on the image of detection result of the false defect rows of the calibration disk is clearly shown distinguishably from a display of other false defect rows. Therefore, it becomes possible to detect a specific size or a specific size range on preferential basis. Further, the regulation itself can be done simply while watching an image of the display screen, without skills. Therefore, the calibration of defect detection sensitivity while watching the detection result on the display screen can be done by any one whose skill is relatively low.

In order to perform a display using defect sizes of one of the false defect rows formed on the calibration disk as a reference, it is possible to provide in a position of the one false defect row a mark capable of displaying the latter false defect row.

In this embodiment, in order to recognize an arrangement of false defects even when the calibration disk itself includes a defect or defects, each false defect row includes at least three recesses or protrusions having substantially the same sizes and adjacent ones of these recesses or protrusions are arranged with a predetermined gap larger than the width of the laser spot in the radial direction.

That is, it is usually rare that a magnetic disk includes three or more real defects arranged in a row with a constant pitch. However, by arranging the false defects with a predetermined pitch larger than the width of the laser spot Sp in the radial direction, it is possible to discretely detect the real defects. Further, even if another defect exists in between false defects in the form of recesses or protrusions, at least two of the false defects arranged in a radial row can be detected, so that the row can be recognized as a false defect row.

FIG. 2(b) illustrates a case where a defect detection signal of a reference disk 1a is detected in a radial direction by the signal processing circuit 41 by scanning the disk which is stationary with a laser spot Sp. Closely spaced 3 waveforms corresponding to 3 false defects fg appear on the defect detection signal. Therefore, it is possible to distinguish a waveform appearing on the detection signal which corresponds to a real defect F in the vicinity of the waveforms from the three waveforms corresponding to the false defects on the basis of a difference in amplitude between the waveform caused by the false defect and that caused by the real defect and a relation between these waveforms.

Contrary to the above mentioned simple regulation of defect detection sensitivity, it is possible to extract a relation between data of detection signal level and a size data of false defect on the basis of a display data stored in the memory 43 of the data processor 44 shown in FIG. 5. That is, since the sizes of defects of the respective false defect rows which are displayed are known, it is enough to obtain data values of the respective sizes. With using the data values, a table of relation between the level and the size of the defect signals is produced.

The relation table is stored in the memory 43 and the level of the detection signal of the signal processing circuit 41 is classified correspondingly to the size of the false defect rows in a detectable size range of the false defect rows by using this table. Therefore, it is possible to calibrate the data of defect size or classified size detected by the surface defect tester 10 more precisely than the case of the previously mentioned conventional calibration. By doing such calibration at the start time of every surface defect test or applying this to a plurality of surface defect testers, it is possible to substantially remove the variation of detection sensitivity occurring every test or occurring between different surface defect testers.

Figure 1C:
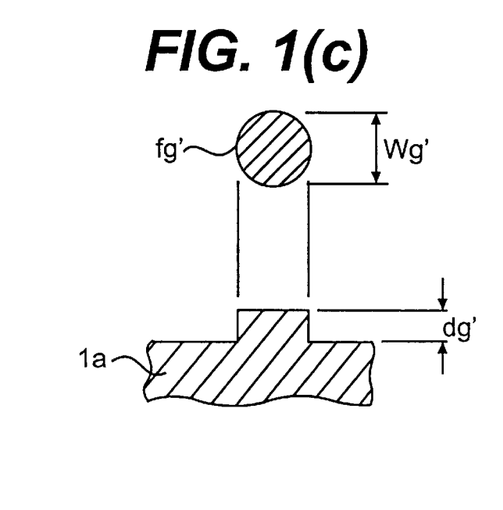
FIG. 1(c) shows a false defect of a false defect row in the form of a circular protrusion.

FIG. 1(c) shows another configuration of false defects in the false defect rows #1 to #12, which take in the form of protrusions fg'.

The size of false defect fg' is selected in the following range, where wg' is a diameter of the false defect and dg' is a height thereof:

Size of False Defect fg'
wg': 0.5 $\mu$m, 1 $\mu$m, 3 $\mu$m, 5 $\mu$m, 10 $\mu$m, 20 $\mu$m
dg': 0.025 $\mu$m, 0.05 $\mu$m, 0.2 $\mu$m, 0.75 $\mu$m, 0.01 $\mu$m Although two kinds of the reference disk having false defects in the form of the circular protrusions and the reference disk having false defects in the form of the square recesses have been described, it is, of course, possible to use a rectangular false defects in lieu of the square false defects or to form circular recesses and square or rectangular protrusions as the false defects.

Although the rectangular recesses (holes) can be formed easily with relatively high precision by an ion beam sputtering device, an arrangement of the rectangular recesses which have a directivity in the radial direction perpendicular to tracks of the disk is relatively difficult when the radius of the disk becomes smaller. Contrary to the rectangular configuration of the false defects, the circular recesses or protrusions have no directivity and can be detected under the same condition even when their radius becomes smaller. However, the formation of recesses or protrusions having right circular shapes is relatively difficult.

Figure 3:
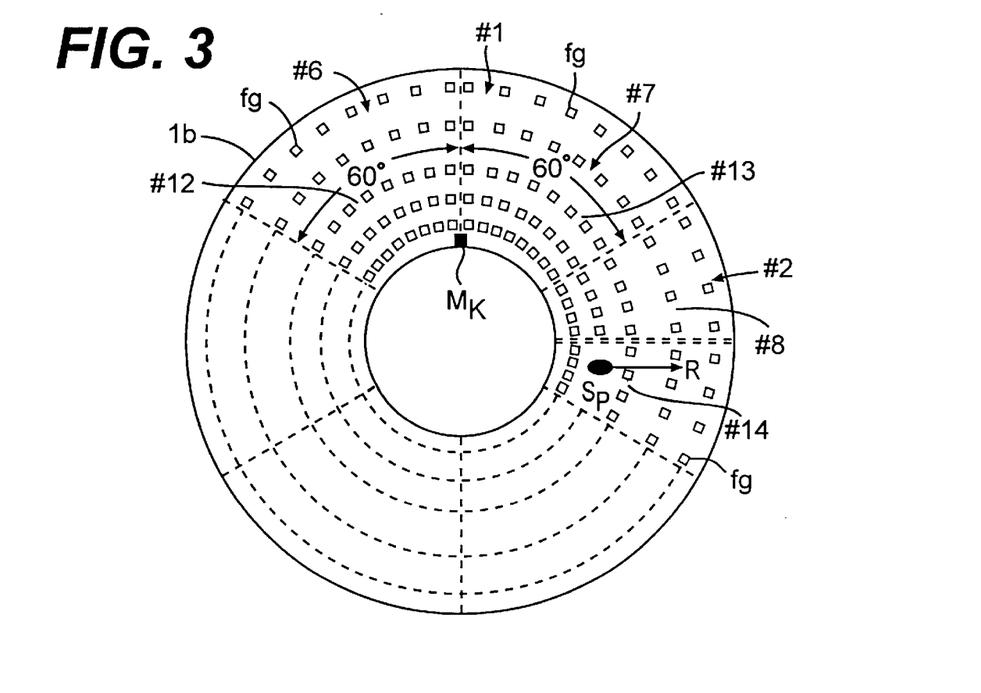
FIG. 3 shows a sensitivity calibration disk according to another embodiment of the present invention.
Figures 4A, 4B:
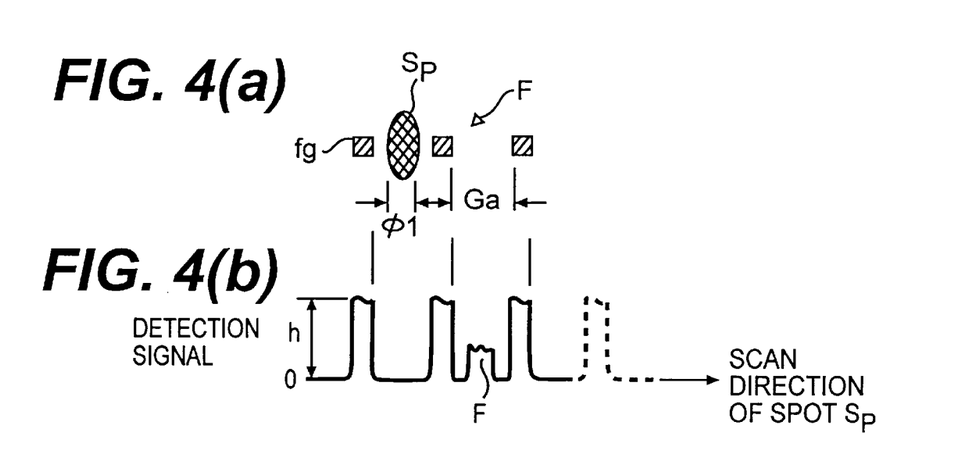
FIGS. 4(a) and 4(b) show a relation between a pitch of the false defects and a scanning laser spot and a detection signal of the false defect, respectively.

FIG. 3 shows a calibration disk 1b which a plurality of coaxially arranged arc rows of false defects fg in the form of square recesses are formed in every 60° sector of the calibration disk. The false defects fg in each row have the same size which is different from those in other rows. The depth of the false defects fg in each row increases successively in clockwise direction. Adjacent false defects fg are separated from each other by a distance Gb larger than a peripheral width $\phi 1$ of a laser spot Sp, as shown in FIG. 4(a). The depth of the respective false defects is selected from the previously mentioned dg or dg'.

The size of the false defects fg in the outermost row is largest and the size thereof is reduced gradually toward the innermost row. The size is selected from the previously mentioned wg or wg'. It is possible to reduce the number of false defects in one row by assigning a smaller size to false defects in an inner row next to the one row. A distance between the coaxial position of the one false defect row and the coaxial position of the inner row next to the one row is sufficiently larger than the radial width (major axis length) $\phi 2$ of the laser spot Sp. FIG. 4(b) corresponds to FIG. 2(b) and shows a detection signal of a false defects fg in the scanning direction of the laser spot Sp. Incidentally, radial dotted lines in FIG. 3 are mark lines provided on the calibration disk 1b for partitioning between the respective false defect rows and are formed by scratchings with using a cutter, etc. Further, a reference position mark Mk can be provided similarly.

Although the present invention has been described with using the mirror-polished disk of aluminum as the reference disk, a disk made of glass may be used as the reference disk. Further, the reference disk may be metal-plated. The reference disk is not limited to a magnetic disk or a substrate thereof and is applicable to any surface detect tester such as a wafer defect tester so long as it tests a surface defect of a circular work while rotating it.

What is claimed is:

1. A calibration disk for calibrating a sensitivity of a surface defect tester which scans a surface of a disk to be tested with a laser spot while moving the laser spot relatively to said disk surface, receives a scattered light of the laser spot by a light receiving element thereof, obtains a detection signal by amplifying an output signal of said light receiving element and outputs, together with a position on the disk, a size of a defect corresponding to a level of the detection signal or a classified size classified correspondingly to the levels of the detection signals on said disk surface, said calibration disk comprising n (n is an integer equal to or larger than 2) equiangularly spaced false defect rows each including 3 or more false defects formed radially or peripherally of said calibration disk, said false defects of each said false defect row being protrusions or recesses having substantially the same size, adjacent ones of said false defects of each said false defect row being physically separated by a predetermined distance larger than a width of a laser spot and the size of said false defects of a certain one of said false defect rows being different from that of said false defects of other said false defect rows.

2. A calibration disk for calibrating a sensitivity of a surface defect tester, as claimed in claim 1, wherein said false defects of each said false defect row are arranged in radial directions and said false defect rows are arranged every predetermined angle.

3. A calibration disk for calibrating a sensitivity of a surface defect tester, as claimed in claim 1, wherein said false defects of each said false defect row are arranged in the peripheral direction and said false defect rows are arranged in peripheral directions every said predetermined angle and in the radial directions spaced by predetermined gap.

4. A calibration disk for calibrating a sensitivity of a surface defect tester, as claimed in claim 2, wherein a size of said false defects of each said false defect row is selected from a range of sizes of defects to be detected and increases or decreases in stepwise along the peripheral direction.

5. A calibration disk for calibrating a sensitivity of a surface defect tester, as claimed in claim 4, wherein the in stepwise increasing or decreasing sizes of said false defects is a size in plan view.

6. A calibration disk for calibrating a sensitivity of a surface defect tester, as claimed in claim 4, wherein the in stepwise increasing or decreasing sizes of said false defects are the same in plan view and are different in depth or height.

7. A calibration disk for calibrating a sensitivity of a surface defect tester, as claimed in claim 4, wherein the in stepwise increasing or decreasing sizes of said false defects are different in plan view and depth or different in plan view and height.

8. A calibration disk for calibrating a sensitivity of a surface defect tester, as claimed in claim 4, wherein a number of said false defects are provided along the radial directions and a mark indicative of a reference position is provided for one of said n false defect rows.

9. A calibration disk for calibrating a sensitivity of a surface defect tester, as claimed in claim 4, wherein said protrusions are formed by performing a sputtering by an ion beam sputtering device through a mask with using tungsten as a target.

10. A calibration disk for calibrating a sensitivity of a surface defect tester, as claimed in claim 4, wherein said false defects have one of square shape, rectangular shape and circular shape and, when said false defects have the square or rectangular shape, one side length of said false defect is selected from a range from 0.5 $\mu$m to 20 $\mu$m and a depth or height thereof is selected from a range from 0.01 $\mu$m to 0.75$\mu$m and, when said false defects have the circular shape, a diameter of said false defect is selected from a range from 0.5 $\mu$m to 20 $\mu$m and a depth or height thereof is selected from a range from 0.01 $\mu$m to 0.75 $\mu$m.

11. A calibration disk for calibrating a sensitivity of a surface defect tester, as claimed in claim 3, wherein the size of said false defect in a position of each said false defect row on said disk is larger than that of said false defect in a next inner position of each said false defect row on said disk.

12. A calibration disk for calibrating a sensitivity of a surface defect tester, as claimed in claim 1, wherein a disk to be tested is a wafer and said calibration disk is formed by forming said false defects on a sample wafer.

\* \* \* \* \*